United States Patent
Bergamaschi

(10) Patent No.: US 6,739,339 B2
(45) Date of Patent: May 25, 2004

(54) SELF-MOISTENING TRACHEOSTOMY DEVICE

(75) Inventor: Paolo Bergamaschi, Concordia sulla Secchia (IT)

(73) Assignee: Bellmafiok S.R.L., Mirandola (IT)

( * ) Notice: Subject to any disclaimer, the term of this patent is extended or adjusted under 35 U.S.C. 154(b) by 24 days.

(21) Appl. No.: 09/988,744

(22) Filed: Nov. 20, 2001

(65) Prior Publication Data

US 2002/0059934 A1 May 23, 2002

(30) Foreign Application Priority Data

Nov. 23, 2000 (IT) .......................... MO20000250

(51) Int. Cl.$^7$ ............................................ A61M 16/00
(52) U.S. Cl. ............................ 128/207.14; 128/201.13; 128/204.17
(58) Field of Search ................. 128/207.14, 207.29, 128/201.13, 206.11, 205.29, 202.27, 203.16, 204.13, 911, 204.17; 623/9

(56) References Cited

U.S. PATENT DOCUMENTS

| | | | | |
|---|---|---|---|---|
| 4,802,474 A | * | 2/1989 | Beevers ................. | 128/200.26 |
| 4,971,054 A | * | 11/1990 | Andersson et al. .... | 128/207.16 |
| 5,022,394 A | | 6/1991 | Chmielinski | |
| 5,035,236 A | * | 7/1991 | Kanegaonkar ......... | 128/201.13 |
| 5,048,518 A | * | 9/1991 | Eliachar et al. ........ | 128/207.14 |
| 5,054,483 A | * | 10/1991 | Marten et al. ......... | 128/207.14 |
| 5,320,096 A | * | 6/1994 | Hans ...................... | 128/205.29 |
| 5,392,775 A | * | 2/1995 | Adkins, Jr. et al. ..... | 128/207.16 |
| 5,485,836 A | * | 1/1996 | Lincoln ................. | 128/206.11 |
| 5,606,966 A | * | 3/1997 | Smith .................... | 128/200.26 |
| 5,636,625 A | * | 6/1997 | Miyagi et al. ......... | 128/200.26 |
| 5,666,950 A | * | 9/1997 | Smith .................... | 128/207.14 |
| 5,701,891 A | | 12/1997 | Groenke | |
| 5,806,515 A | * | 9/1998 | Bare et al. ............. | 128/207.15 |
| 5,840,091 A | * | 11/1998 | Strong ........................ | 55/385.1 |
| 6,105,573 A | * | 8/2000 | Delaplane et al. ..... | 128/200.26 |
| 6,422,235 B1 | * | 7/2002 | Persson ................. | 128/200.26 |
| 2002/0157667 A1 | * | 10/2002 | Fini | |

FOREIGN PATENT DOCUMENTS

| | | |
|---|---|---|
| EP | 0 205 072 A2 | 12/1986 |
| EP | 0 205 072 A3 | 12/1986 |
| WO | WO 99/29268 A1 | 6/1999 |
| WO | WO 99/60954 A1 | 12/1999 |

\* cited by examiner

*Primary Examiner*—Weilun Lo
*Assistant Examiner*—Mital Patel
(74) *Attorney, Agent, or Firm*—Birch, Stewart, Kolasch & Birch, LLP

(57) ABSTRACT

A self-moistening tracheostomy device including a box-like shell having an entry attachment mouth disposed on one side thereof for receiving the end of a tracheostomy cannula, an inlet opening for oxygen administration, and an exchanger element located inside said box-like shell wherein an exchanger element has a plurality of cellulose-type laminar elements.

11 Claims, 2 Drawing Sheets

SELF-MOISTENING TRACHEOSTOMY DEVICE

BACKGROUND OF THE INVENTION

The present invention relates to a self-moistening tracheostomy device.

As is well known, a tracheostomy is an operation designed to implant a temporary or permanent by-pass of the upper airways, i.e. of the nose, mouth, larynx and pharynx, and is carried out to ease the patient's breathing by reducing inspiration and expiration resistance.

Perviousness of the stoma is maintained by means of a cannula inserted into the stoma itself and into the trachea. However, by-passing the upper airways also results in excluding the natural function of these organs, i.e. heating and moistening the air breathed in from the environment before it reaches the lungs. On the other hand, lack of warming and humidification of the air that is breathed in causes in the patients an increase in and a thickening of tracheal secretions with consequent reduction in respiratory efficiency.

To avoid these problems there have for some time been so-called passive humidifiers available that take over the function of the natural organs and the upper airways. Such devices are also known in technical slang as <<artificial noses>> and are designed to be connected to the external attachment of the tracheostomy cannula.

Such known devices consist of a small box-like plastic shell within which is located a hygroscopic material insert, a kind of filter, that absorbs and conserves the moisture and warmth in the exhaled air to then return it to the inhaled air.

Such inserts can be made using essentially two kinds of materials: open cell polyurethane foams or cellulose.

The open cell polyurethane foam type of insert has the advantage of offering low mechanical resistance to the air, thus improving the inhalation and exhalation operations, but is detrimental to the filter capacity to hold and conserve sufficient warmth and moisture.

The cellulose type of insert, on the other hand, holds heat and moisture satisfactorily but with the disadvantage of offering greater resistance to air permeability.

Another feature distinguishing the type of inserts described above is the fact that the inserts obtained with polyurethane foam can be made into any shape that may be necessary as they are permeable in every direction, whereas the cellulose inserts consist of simple helical folds, e.g. in cylindrical form, that for air to pass through must be necessarily housed in a case or box-like shell in such a way that the inhaled and exhaled air flows go through axially and not at right angles, as permeability is inhibited in the latter direction.

The shape of the body case or shell is of great importance in the making of the said artificial noses as these have also to have at least one attachment for an oxygen supply, in case of need, and a valve through which it is possible to intervene, without removing the tracheostomy device, to aspirate any excess secretions.

As a matter of fact, in the tracheostomy devices with a polyurethane foam insert, for example, it is possible to position the oxygen inlet in any area of the case or box-like shell so that the oxygen can pass through the insert from which ever direction it comes, before descending into the lungs, thus taking on moisture and above all heat, as said, in quite limited quantities.

In the case of cellulose inserts, the position of the oxygen inlet is, on the other hand, necessarily located tangentially and externally to the box-like shell since otherwise, i.e. if it were directed towards the inside of the box-like shell, it would be obstructed by the outer surface of the cellulose cylinder that would therefore impede the supply of oxygen.

The two valves similarly pose problems of location as they must be placed in the body of the box-like shell coaxially to the tracheostomy attachment cannula so that any aspiration can be carried out in line and without difficulty.

SUMMARY OF THE INVENTION

The main object of the present invention is that of removing the drawbacks indicated above by providing a self-moistening device for tracheotomies that permits the use of cellulose inserts and therefore a high performance system, with no structural limitations to oxygen inlet and access valve location.

This and other objects that will better appear below are achieved by a self-moistening tracheostomy device according to the present invention that includes a box-like shell and having an entry attachment mouth on one side thereof for the end of a tracheostomy cannula and an inlet opening for oxygen administration, and an exchanger element located inside said box-like shell, characterised in that said exchanger element comprises a plurality of cellulose-type laminar elements.

BRIEF DESCRIPTION OF THE DRAWINGS

Further aspects and advantages of the present invention will better appear from the detailed description of a preferred, but not exclusive, embodiment of a self-moistening device for tracheotomies, illustrated by way of non-limiting example in the accompanying drawings, in which.

DESCRIPTION OF THE PREFERRED EMBODIMENTS

Figure 2:
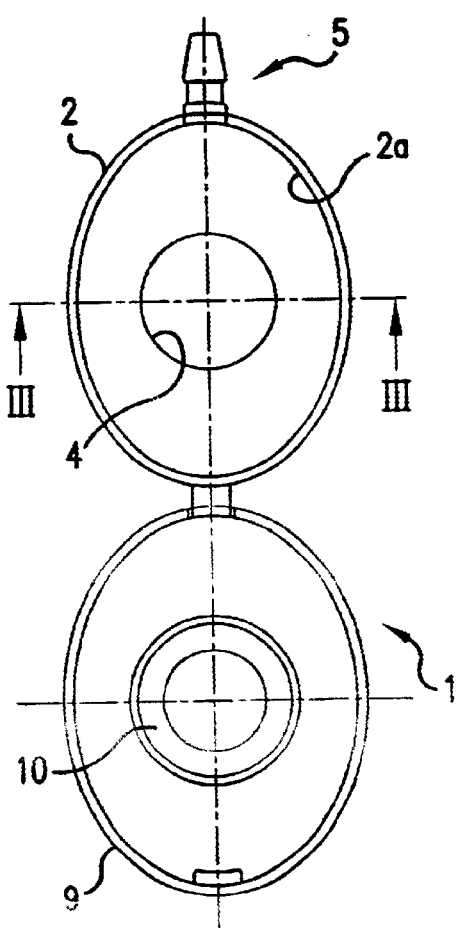
FIG. 2 is a front view of the device of FIG. 1 in its open lid configuration.
Figure 1:
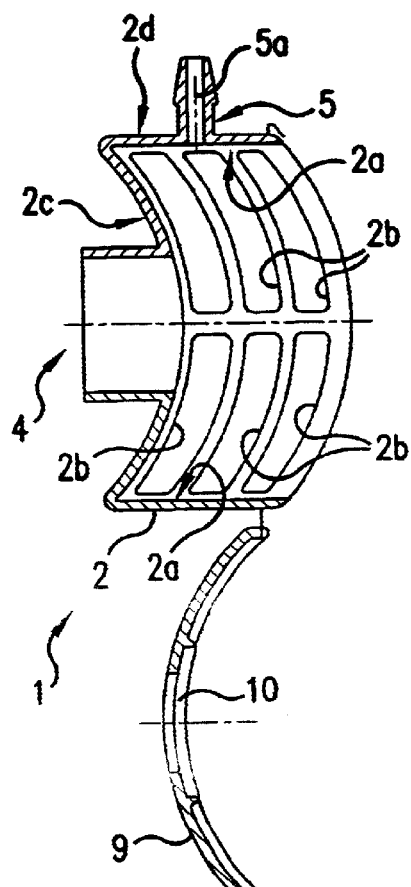
FIG. 1 is a cross-section view of the self-moistening tracheostomy device in accordance with the present invention.
Figure 3:
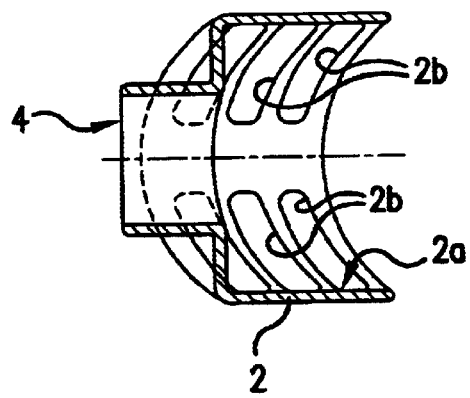
FIG. 3 is a vertical cross-section view taken along the line III—III of FIG. 1.
Figure 4:
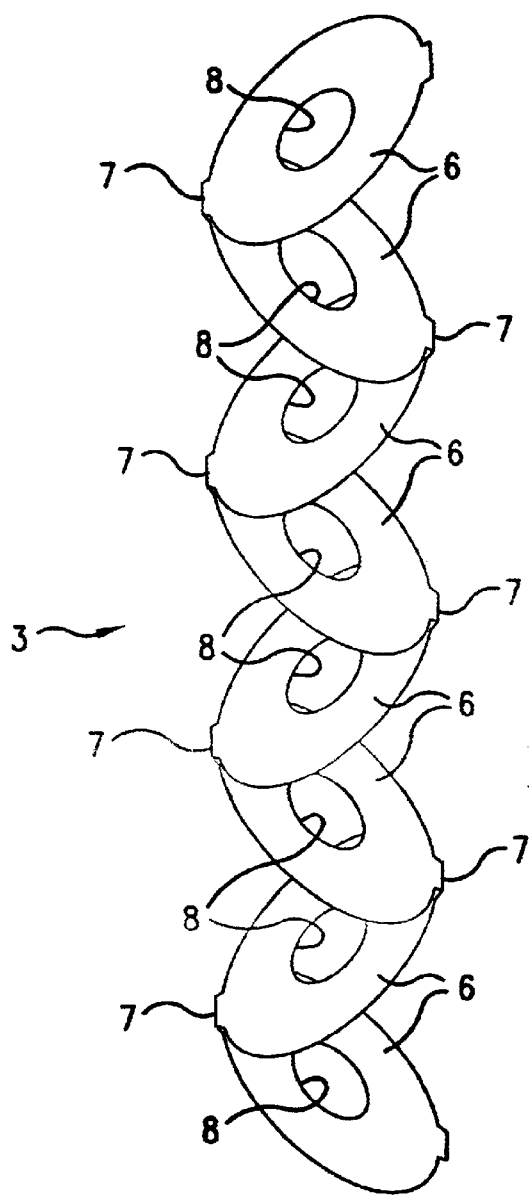
FIG. 4 is a perspective view of a partly distended configuration of an exchanger element that can be inserted into the device in accordance with the present invention.

With reference to the above Figures, reference numeral 1 generally indicates a self-moistening tracheostomy device, which comprises a case or box-like shell 2 inside of which is housed an exchanger element 3.

The device 1 has, formed in its box-like shell 2, an entry opening or mouth 4 for the attachment of the end of tracheostomy cannula (not shown in the drawings), e.g. of any suitable known type, and an inlet opening 5 for the entry of oxygen supply.

The exchanger element 3 comprises a plurality of cellulose laminar elements 6 that are joined to one another at common flaps 7 to form a concertina arrangement.

The inlet opening 5 for the oxygen supply is formed in the side of the box-like shell 2 with its lumen extending substantially tangential to the laminar elements 6 when these are packed inside the cavity 2a of the box-like shell 2.

Figure 5:
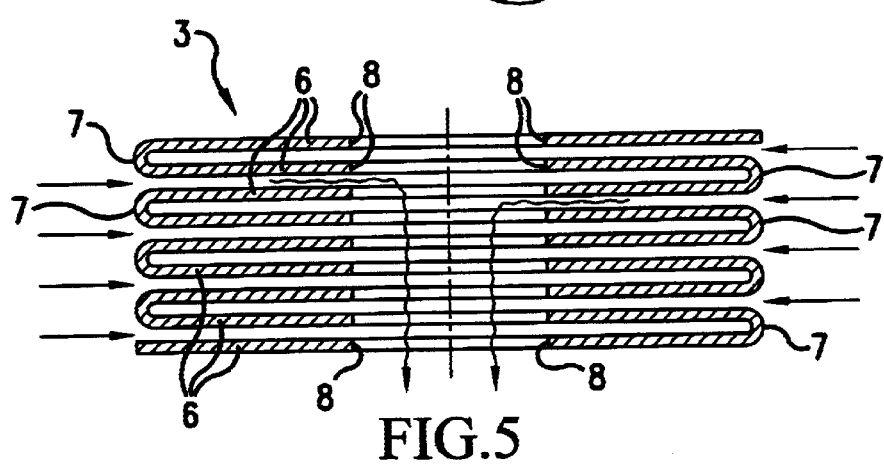
FIG. 5 shows an cross-section view on an enlarged scale of the exchanger element of FIG. 4 packed close for insertion into a case or box-like shell.

The laminar elements 6 are disk-shaped and each axially crossed by a through hole 8 that can be axially aligned with that of the adjacent laminar elements 6 when the latter are packed together (FIG. 5), and with the entry point 4.

The box-like shell 2 has a series of windows 2b on its outer surface that are always open at the front, i.e. on the side opposite that from which the entry mouth 4 juts out of a lid 9 that can open to permit internal access. The lid 9 locates one or more valves 10 for the aspiration of tracheal secretions.

Advantageously, the box-like shell 2 has an ergonomic shape so as to be easily attached to the patient's body to reduce discomfort and disturbance. In practice, in a cross-sectional plan view it is in the form of a circular crown with an elliptical frontal area.

The mouth 4 for attachment of the tracheostomy cannula thus juts out of the concave side 2c of the box-like shell 2 and the inlet opening 5 for the oxygen supply is provided on an essentially flat side 2d thereof.

The working of the above described tracheostomy device according to the present invention is quite simple. The laminar elements 6 are packed together by folding one over the other and then inserted into the cavity 2a in the box-like shell 2 on which the lid 9 is closed.

The various holes 8 are all aligned to each other and to the mouth 4 and the valve 10, whereas the spaces between the laminar elements 6 are arranged to favour the lumen 5a of the inlet opening 5 for the oxygen supply that may be therapeutically required.

The tracheostomy cannula firmly set in place on the patient is then connected to the mouth 4 and the patient's breathing takes place through the device 1, drawing on the air that passes through the outer windows 2b in the surface of the box-like shell 2.

The cellulose from which the exchanger element 3 is made permits good retention of both the heat of the expelled air and its moisture and exchanges them with the inhaled air without problems of mechanical resistance usually associated with cellulose. The passage of air, both on breathing in and breathing out, takes place in a laminar flow through the windows 2b and thus tangentially through the spaces between the various elements 6 that make up the exchanger element 3.

The location on the side of the entry inlet 5 for any oxygen supply that may be necessary, means that the above-described heat and humidity exchange can also be enhanced therewith, this being particularly important as oxygen is usually stored at a low temperature to avoid damaging the patient's respiratory apparatus.

Finally, the valve or valves 10 that is located on the lid 9 permits another cannula to be introduced, if required, into the patient's trachea for aspiration of any excess secretions. When such an operation is not taking place spontaneously, valve 10 keeps its access normally closed, except when there is any overpressure caused by coughing that is released through the valve.

The above described tracheotomy device according to the invention effectively achieves the objects set out above and is susceptible to numerous modifications and variations within the scope of the claims.

What is claimed is:

1. A self-moistening tracheostomy device including a shell having an entry attachment mouth on one side thereof for an end of a tracheostomy cannula, an inlet opening for oxygen administration, and an exchanger element located inside said shell, said exchanger element comprising a plurality of cellulose-type laminar elements, wherein each of said laminar elements has a central through hole in line with said attachment mouth for said tracheostomy cannula.

2. A device according to claim 1, wherein the said cellulose-type laminar elements are joined together in concertina fashion.

3. A device according to claim 1, wherein said inlet opening for supply of oxygen is formed on the side of said shell with its lumen substantially tangential to said laminar elements.

4. A device according to claim 1, wherein said laminar elements are disk-shaped.

5. A device according to claim 1, wherein said shell has frontally on a side opposite said attachment mouth of said tracheostomy cannula an access lid.

6. A device according to claim 5, wherein said lid locates therewithin at least one valve for sucking tracheal secretions.

7. A device according to claim 1, wherein said shell is shaped for being attached to the patient's body.

8. A device according to claim 7, wherein said shell is partly cylindrical in a cross-section plan view and has elliptical sides.

9. A device according to claim 8, wherein said attachment mouth of said tracheostomy cannula juts out of a concave side of said shell and said inlet opening for the administration of oxygen is formed on an substantially flat side thereof.

10. A device according to claim 1, wherein said exchanger element is located within said shell with said laminar elements being packed one upon another.

11. A self-moistening tracheostomy device including a shell and having an entry attachment mouth on one side thereof for an end of a tracheostomy cannula, an inlet opening for oxygen administration, and an exchanger element located inside said shell, said exchanger element comprising a plurality of cellulose-type laminar elements, wherein said shell has, at least on its external surface, a series of constantly open windows.

* * * * *